United States Patent [19]

Carlson

[11] Patent Number: 4,752,223
[45] Date of Patent: Jun. 21, 1988

[54] SHEATH ASSEMBLY FOR DENTAL HANDPIECE

[76] Inventor: Leonard G. Carlson, 15141 Sutton St., Sherman Oaks, Calif. 91403

[21] Appl. No.: 25,608

[22] Filed: Mar. 13, 1987

[51] Int. Cl.$^4$ .............................................. A61C 1/16
[52] U.S. Cl. ................................................... 433/116
[58] Field of Search ............... 433/116; 604/197, 198, 604/199; 128/132

[56] References Cited

U.S. PATENT DOCUMENTS

| | | | |
|---|---|---|---|
| 949,273 | 2/1910 | Hinrichsen | 433/116 |
| 1,093,865 | 4/1914 | Lauderdale | 433/116 |
| 1,470,162 | 10/1923 | Gruss | 433/116 |
| 1,485,963 | 3/1924 | Curry | 433/116 |
| 1,517,186 | 11/1924 | Bond | 433/116 |
| 1,539,253 | 5/1925 | Fuller | 433/116 |
| 2,073,137 | 3/1937 | Bimrose | 433/116 |
| 2,176,339 | 10/1939 | Henneman | 433/75 |
| 2,319,328 | 5/1943 | Kaltenbach | 433/116 |
| 2,429,356 | 10/1947 | Hicks | 433/116 |
| 2,655,725 | 10/1953 | Fehrman | 433/116 |
| 3,299,511 | 1/1967 | Hutson | 433/96 |
| 3,753,292 | 8/1973 | Hutson | 433/96 |
| 4,083,115 | 4/1978 | McKelvey | 433/96 |
| 4,253,831 | 3/1981 | Eaton, II | 433/91 |
| 4,266,935 | 5/1981 | Hoppe | 433/116 |
| 4,279,596 | 7/1981 | Weber | 433/126 |
| 4,286,950 | 9/1981 | Hawk | 433/116 |

Primary Examiner—John J. Wilson
Assistant Examiner—Rohini Sarma
Attorney, Agent, or Firm—Christie, Parker & Hale

[57] ABSTRACT

A sanitary sheath assembly for a dental handpiece comprises a clip removably mountable on the dental handpiece and a disposable sheath mountable over the clip and dental handpiece. The sheath is tubular and has an open proximal end and an operative opening at its distal end. The clip comprises a face plate having an operative opening through which a burr or the like of the handpiece extends. A plurality of fingers extend rearwardly from the face plate for releasably gripping the handpiece. A plurality of tabs extend forwardly from the face plate for engaging the edge of the sheath defining the operative opening of the sheath and for maintaining the operative opening of the sheath in an open arrangement in surrounding relation to the operative opening of the face plate.

16 Claims, 3 Drawing Sheets

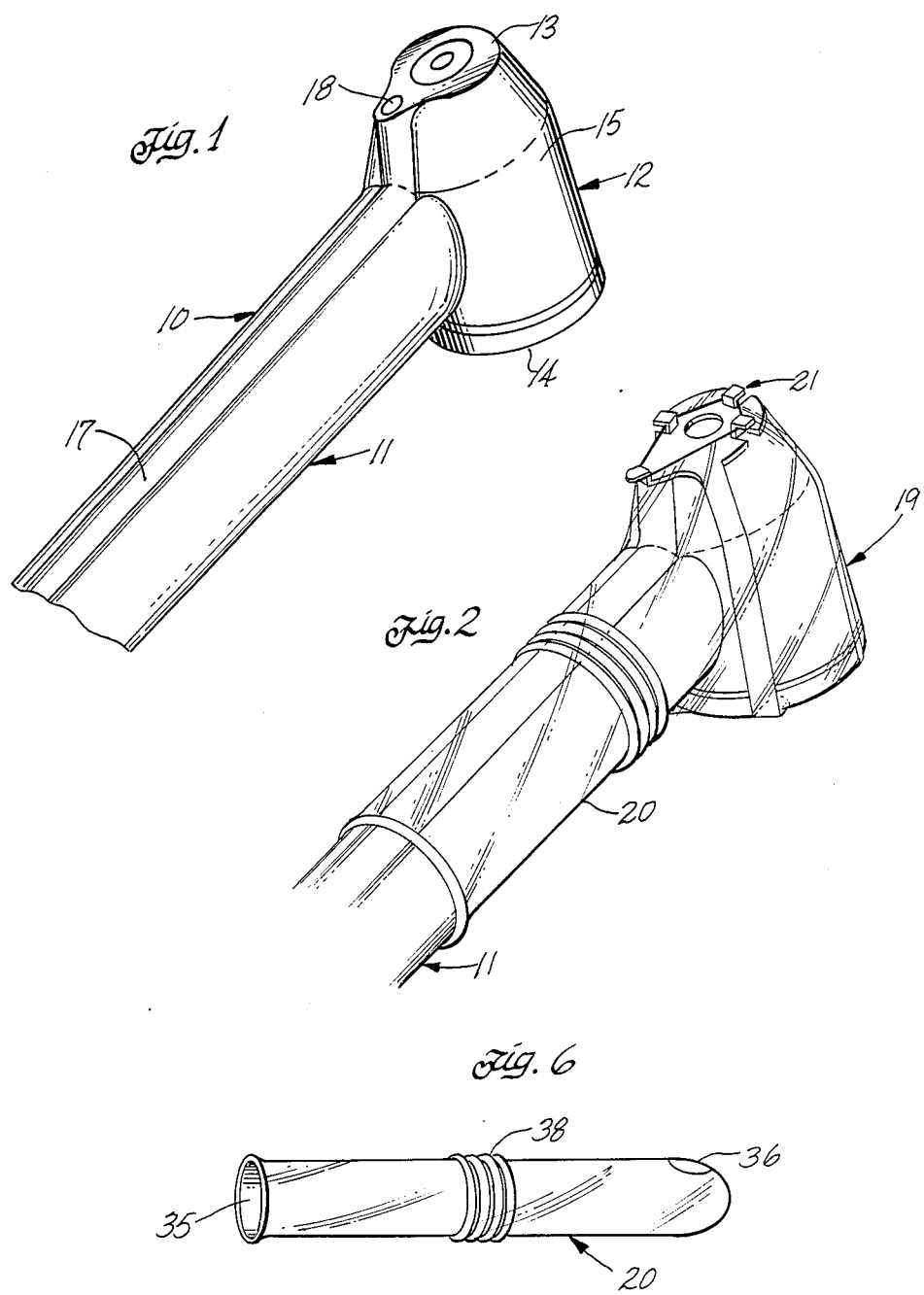

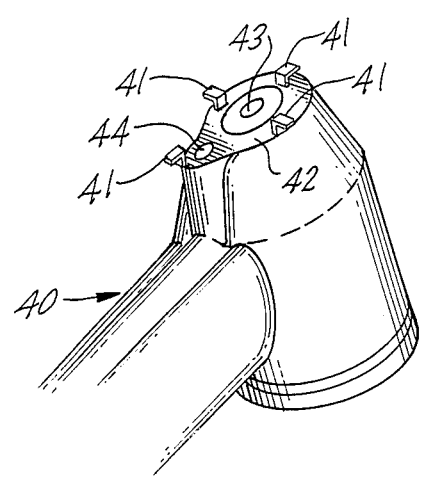

SHEATH ASSEMBLY FOR DENTAL HANDPIECE

FIELD OF THE INVENTION

This invention relates to dental handpieces and more particularly to a sheath assembly including a disposable sheath for a dental handpiece.

BACKGROUND OF THE INVENTION

It is common practice in dental offices to use the same handpiece, e.g., dental drills, in the mouths of all patients. Accordingly, it is important that the handpiece be scrupulously clean to avoid the transmission of disease from one patient to the next. However, modern dental instruments are complex, high precision tools which are difficult to sterilize between patients. Because such high precision instruments are expensive, it is impractical for a dentist to have a sufficient number of sterilized handpieces to accommodate all of his patients.

For the above reason, dental handpieces are usually disinfected between each patient by simply wiping the instruments with a disinfectant such as alcohol. The drawback to this approach is that it does not sterilize the instruments. Moreover, such disinfectants may irritate the skin of the patient.

U.S. Pat. No. 4,266,935 to Hoppe discloses an elastic tubular casing that can be pulled over a dental tool such as a drill or the like to protect it from infectious agents. The casing comprises a protective ring made of hard synthetic resin located at the working end of the dental tool through which the burr extends. The casing is said to be disposal.

U.S. Pat. No. 2,073,137 discloses a sanitary cover similar to that of Hoppe, except that the protective ring is made of metal. Upon removal, the cover may be sterilized by usual methods.

A drawback of the sanitary covers disclosed in the above references is that the covers or casings are of a complex design comprising two dissimilar materials joined together. Such covers are expensive to manufacture. Moreover, because the covers contain a rigid portion, they must be designed for a specific instrument. This means that their use is severely limited.

SUMMARY OF THE INVENTION

The present invention provides a sanitary sheath assembly for a dental handpiece having an operative means such as a rotating burr, light source, water or air passage or the like. The sheath assembly comprises a clip removably mountable on the handpiece and an elongated, disposable flexible sheath mountable over the handpiece and the clip.

The sheath is generally tubular having an open proximal end and a operative opening at its distal end. The clip comprises means for engaging the distal end of the sheath, i.e., the edge of the sheath defining the operative opening, and, when mounted on the handpiece for maintaining the operative opening in surrounding relation to the operative means. The clip further comprises means for removably mounting the engaging means on the dental handpiece.

Preferred means for removably mounting the engaging means on the handpiece comprises a plurality of fingers which extend around at least a portion of the handpiece. Preferred means for engaging the distal end of the sheath and maintaining the operative opening and surrounding relation to the operative means comprises a plurality of tabs which, when the clip is mounted on the handpiece, are spaced apart from and in surrounding relation to the operative means, e.g., burr, of the handpiece.

A preferred embodiment of the invention suitable for use with a dental handpiece having a rotating burr, comprises a clip having a face plate mountable flush against the wall of the handpiece from which the burr extends. The face plate has an opening through which the burr passes and a plurality of forwardly extending tabs generally around the outer periphery of the face plate. The clip further comprises a plurality of rearwardly extending fingers which grip the handpiece and secure the face plate to the handpiece.

In the embodiment, the protective sheath slips over the clip and handpiece with the distal end of the sheath engaging the tabs of the clip which maintain the operative opening of the sheath in an open arrangement spaced apart from the rotating drill burr.

The present invention minimizes contact between the patient and the dental handpiece. After use with one patient, the sheath can be removed and disposed of and the clip can be removed and disposed of or sterilized in a conventional manner. The same clip after sterilization, a previously sterilized clip, or a new sterile clip, can then be mounted on the handpiece. A new sheath can then be slipped over the clip and handpiece. The handpiece is then ready for use with another patient.

BRIEF DESCRIPTION OF THE DRAWINGS

These and other features and advantages of the present invention will be better understood by reference to the following detailed description when considered in conjunction with the accompanying drawings wherein:

FIG. 1 is a perspective view of a dental handpiece suitable for use with the present invention;

FIG. 2 is a perspective view of a sheath assembly made in accordance with the present invention mounted on the dental handpiece;

FIG. 6 is a perspective view of a sheath made in accordance with the present invention; and FIG. 7 is a perspective view of another preferred handpiece.

DETAILED DESCRIPTION

Figure 3:
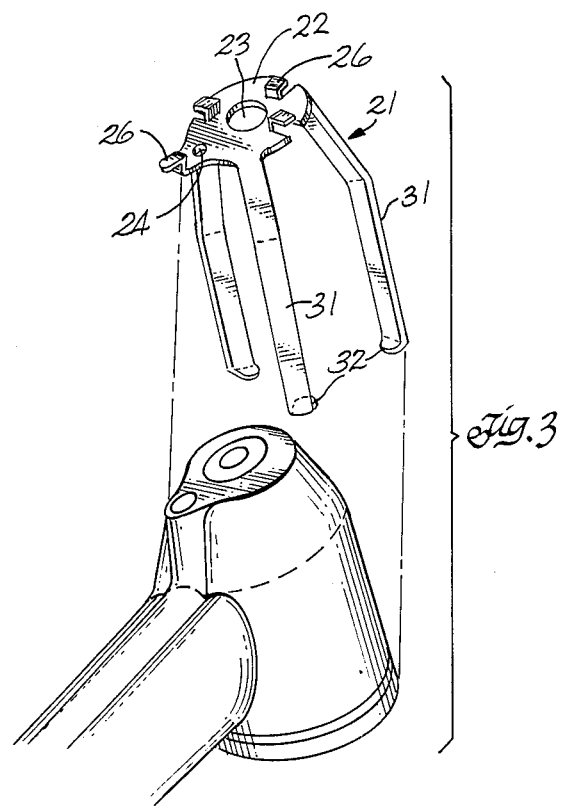
FIG. 3 is an exploded perspective view of the clip and the dental handpiece.

A particularly suitable dental handpiece for use with the present invention is shown in FIG. 1. This handpiece is a high-speed drill in widespread use among dentists for treating cavities. The handpiece 10 is of conventional design and comprises an elongated cylindrical handle 11 and an enlarged head 12 having generally flat front and rear walls 13 and 14 respectively, and a generally cylindrical sidewall 15. The front wall comprises a burr opening 16 for receiving the shaft of a burr. The front wall 13 also comprises an opening 18 through which water is directed at the tooth being drilled to provide cooling. Water is delivered to opening 18 through a conduit 17 running along handle 11 to a water source.

It is understood that the present invention is suitable for use with a dental handpiece having any operative means. As used herein, the term "operative means" is used to denote a functioning mechanism which should not be blocked or covered during use. Examples of operative means include a rotating burr, the open end of a nozzle through which water or air is passed into the patient's mouth, the open end of an aspirator tube through which fluids are removed from the patient's mouth, and light or lamp.

With reference to FIG. 2, there is shown a preferred sheath assembly 19 mounted on a handpiece 10. The sheath assembly 19 comprises a disposal sheath 20 and a clip 21.

Figure 4:
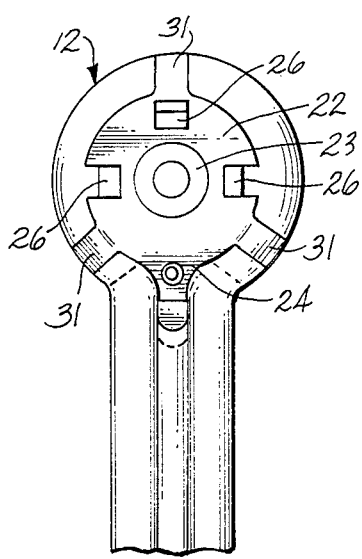
FIG. 4 is a top view of the clip mounted on the dental handpiece.
Figure 5:
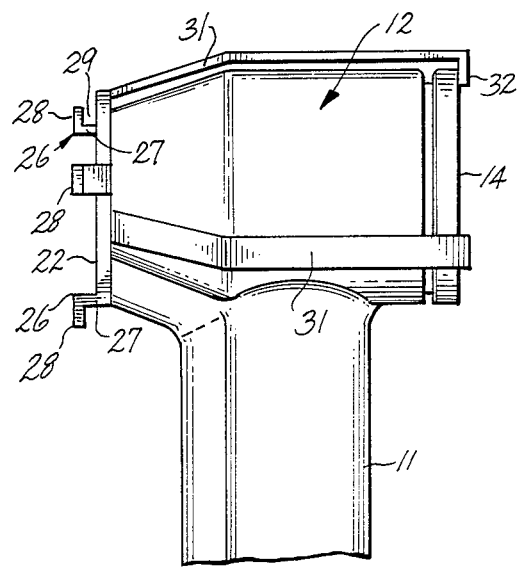
FIG. 5 is a side view of the clip mounted on the dental handpiece.

With reference to FIGS. 3-5, the clip comprises a generally flat, rigid, face plate 22 having a pair of openings including a central burr opening 23 and a water opening 24 and four forwardly extending tabs 26. The face plate 22 is mounted on the handpiece 10 generally flush against the front wall 13 of the enlarged head 12.

The size of the central burr opening 23 is not critical but is preferably selected to provide a small gap between the burr and the face plate 22. This not only enables the burr to rotate freely but enables the dentist to change burrs if desired without removing the sheath assembly. The diameter of the water opening is preferably at least as large as opening 18 so as not to obstruct the water being delivered through the opening.

The tabs 26 are spaced apart from each other in a surrounding relation to the central burr opening 23 and the water opening 24. The tabs 26 are generally rigid and comprise a short first wall 27 which extends forwardly from and generally normal to the face plate 22 and a short second wall 28 which extends laterally outwardly from the end of the first wall 27 remote from the face plate 22. In the embodiment shown, three of the four tabs are located just inside the outer periphery of the face plate 22. For such tabs 26, the second wall 28, first wall 27 and face plate 22 form a generally U-shaped notch 29, as shown in FIG. 5, into which the distal end of the sheath, i.e., the edge of the sheath defining the operative opening of the sheath, is introduced. Such a notch 29 maintains the distal end of the sheath in close contact with the surface of the face plate 22.

In the embodiment shown, there are four tabs. It is apparent that any number of tabs which maintain the operative opening of the sheath in an open arrangement away from the rotating burr and not obstructing the water opening may be used. Further, it is apparent that the tabs may have any suitable size or shape. The tabs 26 are preferably made of the same material as the face plate 22 and are integral with the face plate, but may be made of a different material and joined to the face plate 22 by any suitable means.

Three resilient fingers 31 extend rearwardly from the outer periphery of the face plate 22 along the side wall of 15 of the handpiece head 12. At the rearward end of each finger 31, there is a tang 32 which extends laterally inwardly a short distance across the rear wall 14 of the head 12 of the handpiece 10.

Again, it is apparent that the shape and number of fingers 31 may vary as desired. Like the tabs 26, the fingers 31 are preferably made of the same material of the face plate 22 and integral with the face plate 22, but may be made of a different material and attached to the face plate by any suitable means.

To mount the clip 21 on the handpiece 10, the fingers 31 are spread apart to allow the tangs 32 to clear the sidewall 15 of the handpiece head 12. Once past the sidewall 15, the fingers are released, closing down on the sidewall 15 with the tangs 32 engaging the rear wall 14 and locking the clip 21 on the handpiece 10.

The clip 21 can be made of any suitable non-toxic, generally rigid material with sufficient flexibility and resiliency to enable the clip to be mounted and removed without breakage. Injection molded plastics and non-toxic metals such as stainless steel are presently preferred. If it is desired to sterilize the clips after use, the material of the clip must have sufficient thermal stability to withstand thermal sterilization.

With reference to FIG. 6, the disposable sheath 20 is tubular in structure having an open proximal end 35 and an operative opening 36 at or near its distal end 37. In the embodiment shown, the operative opening 36 is positioned to one side of the distal end of the sheath 20. It is apparent that the operative opening 36 may be located at the distal tip of the sheath or any other suitable location along the length of the sheath. The size and shape of the operative opening 36 is not critical but is preferably selected so that the edge of the sheath defining the operative opening must be stretched slightly to engage all of the tabs 26.

The length of the sheath 20 is not critical but is at least sufficient to cover the portion of the handpiece inserted into the patient's mouth. The diameter of the sheath 20 is selected to allow it to be slipped over the handpiece without difficulty, yet to fit snugly on the handpiece. It is preferred that the sheath be made of thin, flexible, elastomeric material such as latex or the like. The wall thickness of the sheath is not critical but is sufficient to avoid tearing or puncturing during normal use. A thickness of from about 1 to about 5 mils is presently preferred. If desired, the interior surface of the sheath may be coated with a solid lubricant or the like to facilitate mounting of the sheath on the handpiece. Also, if desired, the sheath 20 may comprise a series of circumferential ribs 38 which facilitate gripping of the sheath and handpiece after the sheath has been mounted over the handpiece.

The sheath 20 is slipped over the dental handpiece, conforming generally to the configuration of the handpiece. The distal edge of the sheath defining the operative opening 36 is stretched around and held stationary by the tabs 26. The sheath is sufficiently flexible and movable to allow the dentist to manipulate controls, i.e., buttons, switches, burr changers, and the like, of the handpiece lying beneath the sheath. The sheath is preferably made of a transparent or translucent material also to facilitate manipulation of the controls.

The present invention has the unique advantage of enabling the use of a low-cost truly disposable sheath for a dental handpiece. Such a sheath can be sterilized and packaged in individual packets which remain sealed until the sheath is used. The clips are of a simple design which facilitates their manufacturer and minimizes their cost. The clips may be made of plastic, for example, by injection molding and disposed of just like the sheaths. Alternatively, the clips can be made of a material which can be sterilized. If the latter, a dentist may sterilize a clip between patients or, due to their relatively low-cost, simply keep a stock of clips on hand sufficient to accommodate all of his patients of a particular day and then sterilize all of the clips during the night before the next day's patients arrive.

Another unique advantage of the present invention is that, due to its flexibility and conformability, one sheath may fit a number of differently shaped handpieces. Thus, while different dental handpieces may require differently designed clips, the sheath may be the same. This again, reduces manufacturing costs and hence reduces the overall cost of the protective assembly.

The preceding description has been presented with reference to a presently preferred embodiment to the invention shown in the accompanying drawings. Workers skilled in the art and technology to which this invention pertains will appreciate that alterations and changes in the described structures can be practiced without departing from the spirit principles and scope of this invention.

For example, it is apparent that, any means for engaging the distal end of the sheath and maintaining the operative opening of the sheath in an open arrangement may be used. Rather than a plurality of fingers gripping the handpiece, any means for securing the engaging means to the handpiece may be used.

It is also apparent that, if desired, the engaging means may be attached directly to the dental handpiece, for example, by glue or the like, or may be integral with the handpiece. In such an embodiment, as shown in FIG. 7, the handpiece 40 may comprise a plurality of tabs 41 which extend from the front wall 42 of the handpiece in a surrounding relation to the operative means, e.g., burr opening 43 and water opening 44. This embodiment is not as preferred, however, because the engaging means could not be sterilized.

It is understood that the size and shape of the clip and sheath of the sheath assembly of the present invention may vary to accommodate any dental handpiece.

Accordingly, the foregoing description should not be read as pertaining only to the precise structure described or rather should be read consistent with and as support for the following claims which are to have their fullest fair scope.

What is claimed is:

1. A sanitary sheath assembly for a dental handpiece having an operative means, comprising:
   an elongated tubular sheath having an open proximal end and an operative opening at its distal end, said sheath being removably mountable over the handpiece;
   a clip seperate from the sheath comprising means for engaging the distal end of the sheath and, when mounted on the handpiece, for maintaining the operative opening of the sheath in an open arrangement and in a surrounding relation to the operative means of the dental handpiece, said clip further comprising means for removably mounting the clip on the dental handpiece.

2. A sanitary sheath assembly as claimed in claim 1 wherein the clip comprises a face plate which, when the clip is mounted on the handpiece, is adjacent the operative means.

3. A sanitary sheath assembly as claimed in claim 2 wherein the face plate surrounds the operative means when the clip is mounted on the handpiece and comprises an operative opening positioned so that the operative means is unobstructed.

4. A sanitary sheath assembly as claimed in claim 2 wherein the engaging means comprises a plurality of tabs extending forwardly from the face plate.

5. A sanitary sheath assembly as claimed in claim 4 wherein the tabs comprise a first wall generally normal to the face plate and a second wall which extends laterally outwardly from the end of the first wall remote from the face plate.

6. A sanitary sheath assembly as claimed in claim 4 wherein at least one tab forms a notch adjacent the face plate.

7. A sanitary sheath assembly as claimed in claim 2 wherein the means for removably mounting the engaging means on the dental handpiece comprises a plurality of resilient fingers extending from the face plate around at least a portion of the handpiece.

8. A sanitary sheath assembly as claimed in claim 1 wherein the sheath is made of an elastomeric material.

9. A sanitary sheath assembly as claimed in claim 1 wherein the sheath is made of a material sufficiently flexible to allow manipulation of controls on the handpiece lying beneath the sheath.

10. A sanitary sheath assembly as claimed in claim 1 wherein the sheath is made of a translucent material.

11. A sanitary sheath assembly as claimed in claim 1 wherein the sheath is ribbed to facilitate gripping of the sheath and handpiece when the sheath is mounted on the handpiece.

12. A sanitary sheath assembly for a dental handpiece having an operative means, comprising:
   an elongated, elastomeric, tubular sheath having an open proximal end and a operative opening at its distal end; and
   a clip comprising:
      a face plate having an operative opening;
      means for removably mounting the face plate directly on the handpiece so that the operative opening of the face plate is in surrounding relation to the operative means; and
      means, attached to the face plate, for engaging the edge of the sheath defining the operative opening of the sheath and for maintaining the operative opening of the sheath in an open arrangement in surrounding relation to the operative opening of the face plate.

13. A sanitary sheath assembly as claimed in claim 12 wherein the mounting means comprises a plurality of resilient fingers which extend from the face plate around at least a portion of the handpiece for gripping the handpiece.

14. A sanitary sheath assembly as claimed in claim 12 wherein the engaging means comprises a plurality of tabs which extend forwardly from the face plate.

15. A sanitary sheath assembly as claimed in claim 14 wherein at least one tab forms a notch adjacent the face plate.

16. A sanitary sheath assembly as claimed in claim 12 wherein the sheath is made of latex.

* * * * *